United States Patent [19]

Voerman et al.

[11] 4,188,374

[45] Feb. 12, 1980

[54] ATTRACTANT FOR THE POTATO MOTH AND THE PREPARATION OF THE FORMER

[75] Inventors: Simon Voerman, Wageningen; Cornelis J. Persoons, Delfgauw; Fridolin J. Ritter, Waddinxveen, all of Netherlands

[73] Assignee: Nederlandse Organisatie Voor Toegepast-Natuurwetenschappe-Lijk Onderzoek Ten Behoeve Van Nijverheid, Handel En-Verkeer, The Hague, Netherlands

[21] Appl. No.: 821,954

[22] Filed: Aug. 4, 1977

[30] Foreign Application Priority Data

Aug. 6, 1976 [NL] Netherlands ........................ 7608732

[51] Int. Cl.$^2$ ............................................ A01N 17/14
[52] U.S. Cl. ..................................................... 424/84
[58] Field of Search .......................................... 424/84

[56] References Cited

U.S. PATENT DOCUMENTS 4,010,255  3/1977  Corde et al. ............................ 424/84

OTHER PUBLICATIONS

Roelofs et al., Life Sciences 17, pp. 669–706 (1975).

*Primary Examiner*—Donald B. Moyer
*Attorney, Agent, or Firm*—Brumbaugh, Graves, Donohue & Raymond

[57] ABSTRACT

As attractant for the potato moth (*Phthorimaea operculella*) the novel compound trans-4, cis-7,10-tridecadienyl acetate (2) has been shown to be strongly active, both as such and, still more active, as a synergistic mixture with the known prior art compound trans-4, cis-7-trideca-dienyl acetate (1).

The preparation of the compound (2) is described hereinbelow.

6 Claims, No Drawings

ATTRACTANT FOR THE POTATO MOTH AND THE PREPARATION OF THE FORMER

BACKGROUND OF THE INVENTION

The invention relates to a method for the preparation of an attractant for the potato moth (*Phthorimaea operculella*), as well to a method for the preparation of the active compound trans-4, cis-7, cis-10-tridecatrienyl-acetate applied in this attractant.

The potato moth *Phthorimaea operculella* (Zeller) forms one of the mostly spread pests for the potato growth in many areas of the world. A method that can be applied for combating such types of pests is attracting male moths into a trap by means of a pheromone produced by the female moths.

It was found by H. G. Fouda et al J.Econ. Entomol. 68, pp. 423–427 (1975) that a mixture of 7,11-trideca-dienyl acetates, enriched in the cis, cis-isomere, forms a powerful and specific attractant for the male potato moth. A short time thereafter W. L. Roelofs et al, Life Sciences 17, pp. 699–706 (1975) described the isolation of an attractant from the female potato moths, which substance was identified as trans-4, cis-7-trideca-dienyl acetate, having formula (1) as described hereinbelow. These authors also state that another active substance could be isolated that was not identified however.

SUMMARY OF THE INVENTION

Applicants have now found a further substance having major activity, i.e., trans-4, cis-7, cis-10-trideca-trienylacetate.

Furthermore, it was has been found that this active substance displays a distinctly synergistic effect when it is combined with trans-4, cis-7-trideca-dienyl acetate, a substance already known. As a result it is possible to prepare attractants that contain a mixture of the two substances and that show a considerably raised activity in respect of the natural attractant (1), which is exuded by the female moths.

Consequently, according to the invention, the, method for the preparation of an attractant for the potato moth is characterized in that a mixture of the compounds trans-4, cis-7, cis-10-trideca-trienyl acetate and trans-4, cis-7-trideca-dienyl acetate, in a weight ratio of from 1:10 to 10:1 is brought in a form useful for the application as a attractant.

DETAILED DESCRIPTION OF THE INVENTION

Preferably, in the attractant a mixture is applied in which the weight ratio between trans-4, cis-7, cis-10-trideca-trienyl acetate and trans-4, cis-7-trideca-dienyl acetate amounts to of from 1:1 to 10:1.

Bringing into a form suitable for the application as an attractant can be done in the customary way by mixing the mixture of the two active substances with an inert liquid or solid carrier or substrate. Appropriate carriers or substrates are, e.g. paper, cellulose, rubber, porous foam plastic. Mostly the substrates are allowed to suck up a few drops of a dilute solution of the active mixture containing 50 to 400 μg of the substances and evaporating the solvent.

The synergistic action of the mixture of the two attractants can be shown with the aid of field tests, a number of traps, in which mixtures of a varying composition has been provided, being set in a potato field and the number of male moths caught in them in a certain period of time, being counted. The results of these are shown in the table.

TABLE

| The amount of active substance per trap (μg) | | Number of moths caught in a fortnight. | | |
|---|---|---|---|---|
| t-4,c-7 trideca-dienyl-acetate | t-4,cis-10,cis 7 trideca-trienyl-acetate. | trap 1 | trap 2 | trap 3 | total. |
| 200 | — | 123 | 332 | 307 | 762 |
| 160 | 40 | 606 | 1264 | 931 | 2801 |
| 100 | 100 | 618 | 1321 | 1060 | 2999 |
| 40 | 160 | 674 | 1402 | 1435 | 3511 |
| — | 200 | 275 | 1065 | 614 | 1954 |
| two living females. | | 840 | 463 | — | 1303 |

From these test results it appears clearly that trans-4, cis-7, cis-10 trideca-trienyl acetate per se is over twice as active as trans-4, cis-7-trideca-dienyl acetate and that mixtures of the two compounds show a still better acitivity.

The invention comprises also a method for the preparation of the compound trans-4, cis-7, cis-10-trideca-trienyl acetate, which method has been shown schematically $$CH_3(CH_2)_4CH\overset{c}{=}CHCH_2CH\overset{t}{=}CH(CH_2)_3OCOCH_3 \qquad (1)$$

$$CH_3CH_2CH\overset{c}{=}CHCH_2CH\overset{c}{=}CHCH_2CH\overset{t}{=}CH(CH_2)_3OCOCH_3 \qquad (2)$$

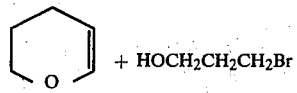
 + HOCH₂CH₂CH₂Br

↓ H⁺

↓ + HC≡CCH₂OH (3)

(4)

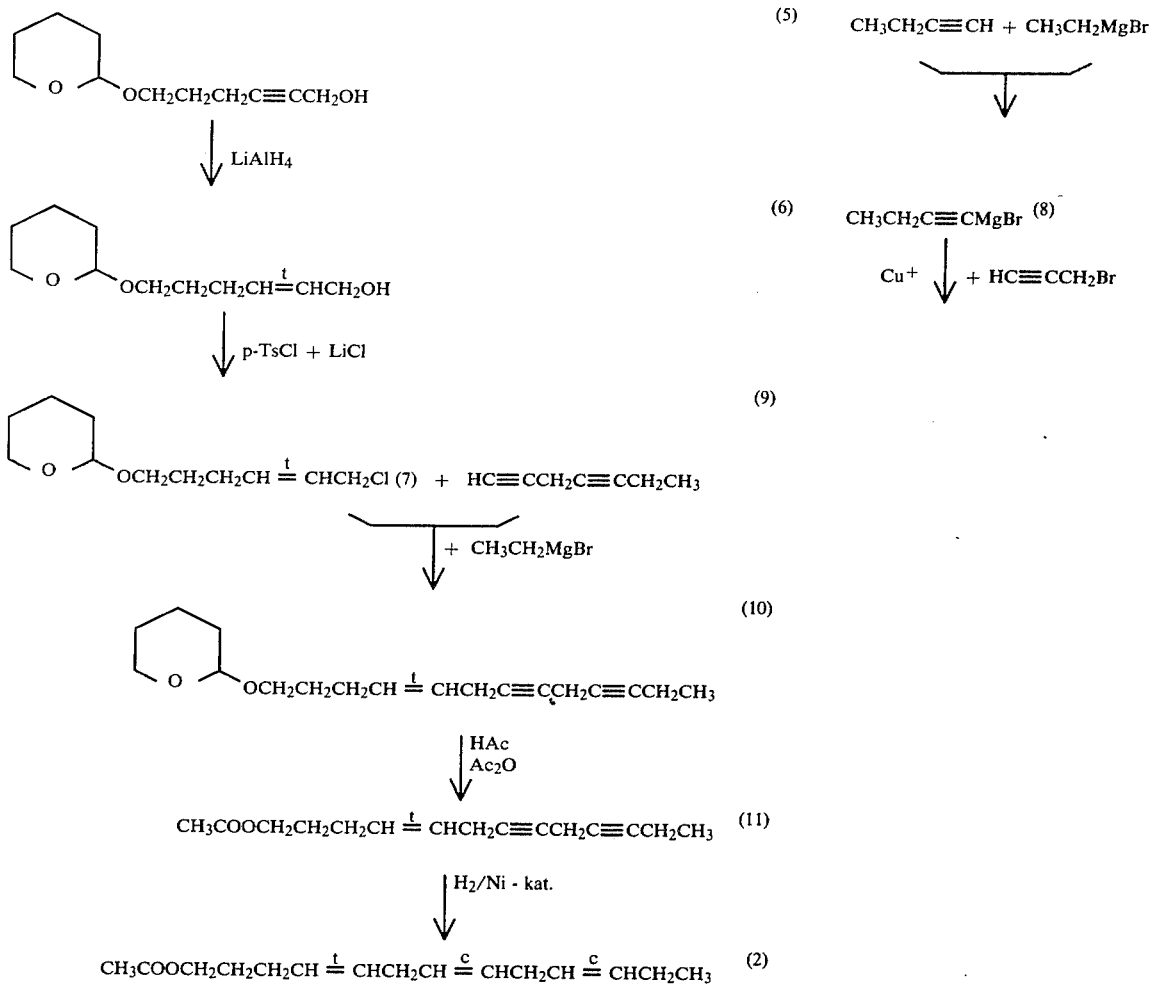

In this method 2-(6-chloro-trans-4-hexenyloxy)tetrahydropyran, having formula (7) is coupled to 1,4-heptadiyn, having formula (9), in the form of a Grignard compound for the formation of 2-(trans-trideca-4-enyl-7,10-diynyl-oxy)-tetrahydropyran, having formula (10). Then this compound is converted into trans-trideca-4-enyl-7,10-diynyl acetate, having formula (11), from which by selective reduction according to a method by Brown et al. J.Chem.Soc.-Chem.Comm. (1973), pp. 553 and J.Org.Chem. 38, pp. 226–2230 the product desired is obtained.

The 2-(6-chloro-trans-4-hexenyloxy)-tetrahydropyran can, for instance, be prepared by firstly coupling 3-bromo-propanol-1, having formula (3), to dihydropyran, thus forming 2-(3-bromopropyloxy)tetrahydropyran, having formula (4). Then from this is obtained by conversion with propargylalcohol, the compound 2-(6-hydroxy-hex-4-ynyloxy)tetrahydropyran, having formula (5).

Next, this compound is reduced to 2-(6-hydroxy-trans-4-hexenyloxy) tetrahydropyran, having formula (6), from which the corresponding 6-chloro-compound is prepared in the way known in the art.

PREPARATION EXAMPLE

The method of preparation is elucidated by means of the non-restrictive example below, showing in a The preparation of compound (7) in b the preparation of compound (9) and in c the preparation of compound (2) from compounds (7) and (9).

a. The preparation of 2-(6-chloro-trans-4-hexenyloxy)tetrahydropyran (7)

70 g (0.83 mol) of dihydropyran were added to a mixture of 79 g (0.57 mol) of 3-bromopropanol-1 and 3 drops of concentrated hydrochloric acid, while it was stirred and cooled, and the temperature being kept at approximately 28° C.

After the mixture had been stirred for a night at ambient temperature, it was heated for another 5 hours at 25° C.

The yellow-orange mixture obtained was extracted with diethyl ether and the ether extract was washed out with a saturated $NaHCO_3$ solution and thereupon with a 20% solution of sodium chloride in water.

The oil obtained after evaporation of the solvent was distilled in vacuum and yielded 94 g (74%) of 2-(3-bromo propyloxy)tetrahydropyran; bp. 66° C./0.6 mm.

Into a three-necked flask of 2 liters content were brought 600 ml of $NH_3$ and to this were added 200 mg of Fe $(NO_3)$ 3.9 $H_2O$, while the mixture was stirred. After a quarter of an hour 6.1 g (0.88 mol) of lithium were added in small portions, and when the blue colour had disappeared, 24.4 g (0.44 mol) of propargyl alcohol in the course of half an hour.

After the mixture had been stirred for another 1.5 hours, next, rather quickly a solution of 62.4 g (0.28 mol) of the above bromium compound in 250 ml of dry tetrahydrofuran were added.

The mixture was stirred for a night at ambient temperature, thereupon 600 ml of water were added and then it was extracted with diethyl ether (5×100 ml).

The extract was washed with a 20% solution of NaCL, dried over $MgSO_4$ and then distilled in vacuum; bp. 99° C./0.01 mm, yield: 45.4 g (82%). Of the 2-(6-hydroxy-hex-4-ynyloxy)tetrahydropyran) obtained 24.8 g (0.125 mol) in 130 ml of dry diethyl ether were rather quickly added to a stirred suspension of 4.3 g of lithium aluminium hydride in 90 ml of dry diethyl ether under nitrogen, cooled at −80° C.

After some hours the cooling bath was removed and the mixture firstly reheated up to ambient temperature and then refluxed for 3.5 hours. The mixture was kept for 48 hours at ambient temperature, whereupon 12 ml of ethylacetate were added and then 250 ml of a saturated $NH_4Cl$ solution and 200 ml of a 20% NaCl solution.

Finally the mixture was extracted with diethyl ether, the extract was washed up to neutral with a 20% NaCl solution, dried over $MgSO_4$ and then distilled in vacuum; bpt 87°–88° C./0.02 mm Hg, yield 19.2 g (77%) of compound (6).

Under nitrogen 18.5 g (92.5 mmol) of the 2-(6-hydroxy-trans-4-hexenyloxy)-tetrahydropyran was brought in a mixture of 50 ml of dry diethyl ether and 25 ml of hexamethyl phosphoric acid triamide (HMPT) and then at a temperature below 0° C. 50 ml of a 20% solution of butyl lithium in hexane were added so that a wine-red colour was produced.

The mixture was reheated up to ambient temperature, whereupon a solution of 19.1 g of p-toluene sulphonyl chloride (TsCl) in 50 ml of dry diethyl ether and 25 ml of HMPT were added in 10 minutes, the temperature being kept below 16° C. Then 13 g of dry lithium chloride were added and after the mixture had been stirred for 20 minutes the thin sludge obtained was poured into 230 ml of ice-water and extracted with diethyl ether (5×50 ml). The extract was washed with 20% NaCl solution; dried ($MgSO_4$) and distilled in vacuum, the product desired being obtained, having a bp. of 84° C./0.10 mm Hg. Yield: 16 g (79.26%) of compound (7).

b. The preparation of 1.4-heptadiyn (9)

In a three-necked flask of 1 liter content firstly ethyl magnesium bromide was prepared, under nitrogen, from 13 g (0.54 mol) of magnesium and 53 g (0.50 mol) of ethyl bromide in 200 ml of tetrahydrofuran. Then butyn-1 is passed at a rate of approximately 100 ml/min, for 2.5 hours, the mixture being cooled with ice water. Thereupon it was heated for another quarter of an hour at 60° C., the passing into of nitrogen being continued. The mixture obtained, containing butyn-1-ylmagnesium bromide, having formula (8) of the formula sheet was decanted in a second three-necked flask, and under nitrogen firstly 2 g of freshly dried CuCl and then rather quickly 45 g (0.38 mol) of freshly distilled 3-bromo-propyn-1 were added to it. After it had been stirred for a night, the mixture was poured into water in which 40 g of $NH_4Cl$ and 5 g of KCN had been dissolved. The whole was extracted with diethyl ether (5×50 ml), the extract was washed to neutral with a 20% NaCl solution, dried ($MgSO_4$) and distilled, the product desired being obtained, having a bp. of 54° C./5.5 cm mercury. Yield 22 g (63%).

c. The preparation of trans-4,cis-7,cis-10-trideca-trienylacetate (2)

In a similar way as described under b, ethyl magnesium bromide was prepared from 4.4 g (40 mmol) of ethyl bromide and 1.0 g (40 mmol) of magnesium in 30 ml of diethyl ether under nitrogen. To this 2.7 g (30 mmol) of 1,4-heptadiyn were added and the mixture was heated at 40° C., gas being evolved.

After the reaction had been completed the yellow-coloured mixture was filtered and in a nitrogen atmosphere added to 6.6 g (30 mmol) of 2-(6-chloro-trans-4-hexenyloxy)tetrahydropyran) in 20 ml of diethyl ether to which also 0.5 g of CuCl had been added. A strongly exothermic reaction occurred, a system being formed consisting of two layers.

After approximately 2 hours, 40 ml of dry tetrahydrofuran, were added whereupon the mixture, while being stirred, was kept at ambient temperature for one night. Then 50 ml of a saturated $NH_4Cl$ solution and 2 g of KCN were added and the mixture was extracted with diethyl ether. The extract was washed with a 20% NaCl solution to neutral, dried ($MgSO_4$) and evaporated, 8.2 g of an oil remaining.

With 40 ml of glacial acetic acid and 20 ml of acetic acid anhydride the oil obtained was converted into the acetate, which after distillation was recovered in an amount of 1.5 g, as a fraction boiling at 115°–120° C./0.03 mm of mercury.

The reduction of the acetate was carried out with hydrogen in the presence of a nickel catalyst.

For this purpose, to 1.25 g of Ni $(OCOCH_3)_2.4H_2O$ in 50 ml of ethanol under hydrogen, were added 5.0 ml of a sodium boric hydride solution (obtained from 1 g of $NaBH_4$, 24 ml of ethanol and 1.25 ml of 2 N sodium hydroxide solution and filtration of the mixture) and then another 0.7 ml of 1.2-diamino ethane.

After the hydrogen absorption had been completed (234 ml) the mixture was filtered, the filtrate diluted with 200 ml of a 20% NaCl solution and thereupon extracted with diethyl ether.

The extract was washed with a 20% NaCl solution, dried over $MgSO_4$ and evaporated, 1.1 g of a yellow liquid being obtained.

According the NMR spectral analysis the structure of this compound was found to agree with trans-4, cis-7,cis-10-trideca-trienyl acetate.

We claim:

1. An attractant for the potato moth (*Phthorimaea operculella*), an active ingredient of which essentially consists of a mixture of trans-4, cis-7, cis-10-tridecatrienyl acetate and trans-4, cis-7-tridecadienyl acetate in a weight ratio of from about 1:10 to about 10:1.

2. An attractant according to claim 1, wherein the weight ratio of said trienyl acetate to dienyl acetate is from about 1:1 to about 10:1.

3. An attractant according to claim 1 in combination with an inert solid or liquid carrier or substrate.

4. In a method for control of the potato moth (*Phthorimaea operculella*) which comprises subjecting said moth to an attractant in an amount sufficient to attract the moth, the improvement comprising the use, as said attractant, of an effective amount of the attractant according to claim 1.

5. A method according to claim 4, wherein said attractant is used in an insect trap which is located in an area which is to be protected against said moth.

6. A method according to claim 4, wherein said attractant is used to permeate the air in, around or over an area which is to be protected against said moth.

* * * * *